(12) United States Patent
Birnkrant

(10) Patent No.: US 9,107,573 B2
(45) Date of Patent: Aug. 18, 2015

(54) DETACHABLE SHAFT FLEXIBLE ENDOSCOPE

(71) Applicant: Dashiell A. Birnkrant, Worcester, MA (US)

(72) Inventor: Dashiell A. Birnkrant, Worcester, MA (US)

(73) Assignee: KARL STORZ ENDOVISION, INC., Charlton, MA (US)

( * ) Notice: Subject to any disclaimer, the term of this patent is extended or adjusted under 35 U.S.C. 154(b) by 25 days.

(21) Appl. No.: 13/654,123

(22) Filed: Oct. 17, 2012

(65) Prior Publication Data

US 2014/0107416 A1    Apr. 17, 2014

(51) Int. Cl.
*A61B 1/04*       (2006.01)
*A61B 1/005*      (2006.01)
*A61B 1/00*       (2006.01)

(52) U.S. Cl.
CPC ............. *A61B 1/00114* (2013.01); *A61B 1/005* (2013.01); *A61B 1/00016* (2013.01); *A61B 1/00066* (2013.01); *A61B 1/00105* (2013.01); *A61B 1/00124* (2013.01); *A61B 1/00032* (2013.01)

(58) Field of Classification Search
CPC ........................ A61B 1/00105; A61B 1/00066
USPC ......... 600/131, 132, 136, 172, 154, 156, 159, 600/110; 348/45
See application file for complete search history.

(56) References Cited

U.S. PATENT DOCUMENTS

| | | | |
|---|---|---|---|
| 4,534,339 A | 8/1985 | Collins et al. | |
| 4,696,544 A | 9/1987 | Costella | |
| 4,905,082 A | 2/1990 | Nishigaki et al. | |
| 4,911,148 A | 3/1990 | Sosnowski et al. | |
| 4,971,034 A * | 11/1990 | Doi et al. | 600/104 |
| 5,349,942 A | 9/1994 | Heimberger | |
| 5,609,561 A | 3/1997 | Uehara et al. | |
| 5,621,830 A | 4/1997 | Lucey et al. | |
| 5,630,795 A * | 5/1997 | Kuramoto et al. | 604/30 |
| 5,807,238 A * | 9/1998 | Feldman et al. | 600/133 |
| 5,846,183 A | 12/1998 | Chilcoat | |
| 6,004,263 A | 12/1999 | Nakaichi et al. | |
| 6,527,707 B1 * | 3/2003 | Frische et al. | 600/153 |

(Continued)

FOREIGN PATENT DOCUMENTS

| | | |
|---|---|---|
| EP | 1666864 A1 | 6/2006 |
| EP | 2055223 A1 | 5/2009 |

(Continued)

OTHER PUBLICATIONS

European Search Report Application No. EP 13 18 8487 Completed: Feb. 13, 2014; Mailing Date: Feb. 24, 2014 17 pages.

*Primary Examiner* — Anhtuan T Nguyen
*Assistant Examiner* — Timothy J Neal
(74) *Attorney, Agent, or Firm* — Whitmyer IP Group LLC

(57) ABSTRACT

A flexible endoscope includes a handle, a flexible shaft having a distal end and a proximal end, a coupling mechanism releasably attaching the handle to the distal end of the flexible shaft, an illumination unit disposed in the flexible shaft, the illumination unit providing light to an area in front of the distal end of the flexible shaft, and an imaging unit disposed in the flexible shaft, the imaging unit generating image data of the area in front of the distal end of the flexible shaft, wherein the coupling mechanism includes an electrical channel for transmitting electrical power to the illumination unit and the imaging unit, and a data channel for transmitting the image data from the imaging unit.

26 Claims, 7 Drawing Sheets

(56) References Cited

U.S. PATENT DOCUMENTS

| | | |
|---|---|---|
| 6,875,169 B2 | 4/2005 | Berci et al. |
| 7,212,737 B2 | 5/2007 | Dehmel et |
| 7,384,308 B2 | 6/2008 | Boehnlein et al. |
| 7,581,988 B2 | 9/2009 | Boehnlein et al. |
| 7,584,534 B2 | 9/2009 | Pease et al. |
| 7,918,788 B2 | 4/2011 | Lin et al. |
| 7,942,813 B2 | 5/2011 | Mackin |
| 8,167,790 B2 * | 5/2012 | Kucklick et al. ............... 600/114 |
| 2006/0196250 A1 * | 9/2006 | Gocho ............................... 73/40 |
| 2007/0129604 A1 | 6/2007 | Hatcher et al. |
| 2008/0214896 A1 | 9/2008 | Krupa et al. |
| 2008/0249355 A1 | 10/2008 | Birnkrant et al. |
| 2008/0255424 A1 * | 10/2008 | Durgin et al. .................. 600/156 |
| 2009/0018392 A1 | 1/2009 | Scholly et al. |
| 2009/0225159 A1 | 9/2009 | Schneider et al. |
| 2010/0022829 A1 | 1/2010 | Irion et al. |
| 2010/0087708 A1 | 4/2010 | Chen et al. |
| 2010/0191053 A1 | 7/2010 | Garcia et al. |
| 2011/0130627 A1 | 6/2011 | McGrail et al. |
| 2012/0157771 A1 * | 6/2012 | Avitsian et al. ................ 600/125 |

FOREIGN PATENT DOCUMENTS

| | | |
|---|---|---|
| WO | 02055126 A2 | 7/2002 |
| WO | 2008063565 A2 | 5/2008 |
| WO | 2008086497 A1 | 7/2008 |

* cited by examiner

DETACHABLE SHAFT FLEXIBLE ENDOSCOPE

FIELD OF THE INVENTION

This invention relates to an endoscope, and more specifically to a detachable shaft flexible endoscope having a coupling mechanism which releasably attaches a flexible shaft to a handle and provides operable connections for internal components of the flexible shaft to the handle.

BACKGROUND OF THE INVENTION

Endoscope technology has advanced significantly since its initial creation. Early endoscopic devices included a rigid, substantially linear shaft permanently attached to a handle, a light delivery system extending from the shaft to the handle and receiving light from an external source, and a plurality of optical lens for transmitting an image to an eyepiece. Since then, the endoscope has grown increasingly complex, incorporating a flexible shaft, a shaft with a working channel for communicating fluids or medical tools, mechanical components extending from the handle to articulate the shaft, a light source embedded within the handle, optical fiber bundles for transmitting an image from a distal end of the shaft to an eyepiece on the handle, and/or distal imagers.

However, as the endoscope becomes more complex, component failure and failure due to damage also increases, especially with regard to fragile components positioned within the shaft section of the endoscope. This is particularly true for flexible endoscopes, wherein delicate components within the flexible shaft, including the outer sheath, may be subjected to excessive bending, twisting, coiling, and fluid contamination. When one of these internal components is damaged or fails, the entire endoscopic device requires extensive repair. Both shaft and handle must be sent to a medical device manufacturer for repair. This requires a significant amount of down time (e.g., repair time, shipping time to and from the manufacturer) in which the medical practitioner/surgeon is without the endoscope. To minimize the inconvenience, the surgeon can request a loaner-endoscope from the medical device manufacturer. However, this option still involves some downtime and requires that the surgeon pay extra fees for renting the loaner-endoscope in addition to paying the costs of repairing the damaged endoscope.

In order to resolve or minimize the inconveniences associated with repairing broken endoscopes, endoscope designs have been developed in which sections of the endoscope (e.g., shaft, handle, illumination unit) can be detached by the physician. One such approach is described in U.S. Pat. No. 4,905,082 to Nishigaki et al. Nishigaki discloses a rigid endoscope comprising a rigid shaft fixedly attached to an operating section (handle), wherein the operating section has a connection ring for connecting an imaging unit thereto. The endoscope does not allow the shaft to be separated from the handle and instead provides for the imaging unit to be detachable. This design of the endoscope has significant drawbacks. The shaft is rigid and is not as maneuverable in tight areas of a body cavity as a flexible, articulating shaft. The endoscope also requires a rod lens system disposed in the shaft to transfer an optical image to the imaging unit. If there was a problem with the endoscope capturing an image, it may not be readily apparent to the surgeon whether the rod lens system in the shaft and/or the imaging unit was causing the problem. Therefore, both the shaft (with the handle) and the imaging unit would still have to be sent for diagnosis and repair. Moreover, the endoscope comprises a light guide which extends from the handle into the shaft and receives light from an external source. If the light guide is damaged, then the entire endoscope—shaft and handle—has to be sent for repair.

U.S. Pat. No. 4,911,148 to Sosnowski et al. describes an endoscope having a flexible shaft which deflects along an end segment and detaches from a handle. However, the shaft is designed such that an optical image fiber within a fiber post extends outside of the main housing of the shaft. The optical image fiber, therefore, is exposed and susceptible to damage during the process of attaching/detaching the shaft to the handle. Further, with the deflection mechanism being positioned in the shaft and a deflection control ring being mounted on the handle, an interface adapted for mechanical movement is required at the shaft-handle attachment. Dynamic seals are needed to enclose the two sections of the endoscope. However, dynamic seals have a finite lifetime and are prone to wear and leakage. Both shaft and handle lack the capability to detect any leaks and discharge any fluids that enter into their interiors. Moreover, the endoscope is configured such that an image is transferred from the optical image fiber in the shaft to an optics module and eyepiece in the handle. If a distorted image was displayed at the eyepiece, the problem could be caused by damage to either the optical image fiber or the optics module. As a result, both the shaft and the handle would still have to be sent to the manufacturer for proper diagnosis and repair.

Other efforts have been made to provide an endoscope with detachable means to release and couple a handle to a shaft. For example, U.S. Pat. No. 6,004,263 to Nakaichi et al. discloses an endoscope having a handle attached to a flexible shaft via a coupling unit. Still, the endoscope includes an optical system, where a handle-mounted eyepiece is used for viewing optical images that are gathered by an objective lens in the distal end of the shaft and transmitted through an optical fiber bundle to a lens assembly in the handle. Like the above prior art, it would not be readily apparent which optical component is the cause of the problem and therefore both the handle and the shaft must be sent for diagnosis and repair. Nakaichi also discloses the endoscope having operating wires to articulate the shaft. In order to interface the operating wires to a control unit on the handle, a mechanism separate from the coupling unit is provided. This mechanism is disposed on the outer surfaces of the shaft and handle and requires that the wires be exposed outside the shaft body. The shaft, therefore, fails to be completely sealed and cannot prevent leakage of fluid into the interior of the shaft. In addition, the shaft fails to include a device for detecting and removing fluid therein.

U.S. Patent Application Publication No. 2010/0191053 to Garcia et al. discloses an articulating endoscope comprising a detachable operator control section, which has a cable wire control system, and a plurality of flexible shaft assemblies. In one embodiment, the endoscope has a handle-mounted eyepiece attached to an optical fiber bundle in the shaft. The shaft is designed with an extreme section extending beyond and outside the shaft's main body, wherein the extreme section is inserted into a cavity in the handle. Within the extreme section are optical image fibers and pull wires. This design has significant drawbacks. The extreme section, which contains delicate components of the endoscope, is exposed and susceptible to damage during attachment/detachment of the shaft into the handle. The shaft and handle also require dynamic seals to accommodate for the interface between the pull wires in the shaft and a handle-mounted steering lever. Because of the drawbacks of dynamic seals, the interiors—and internal components—of the handle and shaft are susceptible to damage and/or contamination by fluid leaking therein.

None of the above prior art references discloses a detachable shaft flexible endoscope having a design which is not prone to damage during attachment and detachment of the shaft to and from the handle. Further, the endoscopes fail to provide sufficient sealed enclosures for the shaft and handle when detached from each other and lack any means for detecting fluid leakage. The above references also teach endoscopes with optical systems comprising multiple optical lenses disposed in both the handle and the shaft. Accordingly, delicate components are located within both sections of the endoscope, thereby requiring that the handle and shaft be sent for repair when a malfunction occurs.

It is therefore desired to provide a flexible endoscope having a design which provides easier diagnosis and repair of internal components and minimizes the inconveniences associated with repair downtime. It is also desired to provide a detachable shaft flexible endoscope having a coupling mechanism for releasably attaching a flexible shaft to a handle, wherein delicate components are housed safely within the main body of the shaft and/or handle and do not extend or protrude out. It is further desired to provide a detachable and articulating shaft endoscope, wherein the handle and shaft are both protected from fluid leakage—especially at the handle-shaft attachment—when in an attached and detached configuration.

SUMMARY OF THE INVENTION

Accordingly, it is an object of the present invention to provide an endoscopic instrument having a handle and a flexible shaft, wherein the flexible shaft can easily be attached and detached from the handle. Related to this object, the endoscope should be configured such that the internal components that are fragile and delicate are concentrated in one section of the instrument.

It is a further object of the present invention to provide an endoscope having a flexible shaft adapted to detachably engage a handle such that an interface, or operative connection, is established between the internal components within the flexible shaft and the internal components within the handle.

It is yet another object of the present invention to provide a flexible endoscope having a handle and a detachable flexible shaft, wherein the handle and the shaft are each adapted to prevent and/or reduce the likelihood of contamination (from fluids, germs, bacteria) of their internal components when in a detached configuration. It is also an object to provide an endoscope, wherein, when the handle and flexible shaft are coupled to each other, they collectively prevent and/or reduce the likelihood of contamination of their internal components and the interface between each section of the endoscope.

It is still another object of the present invention to provide an endoscopic instrument having a detachable flexible shaft which is modular and can releasably couple and interface with one of a plurality of handles, wherein each handle has different functions, capabilities, and/or auxiliary devices attached or in communicative relation thereto.

These and other objects of the invention are achieved by providing a detachable shaft flexible endoscope including a handle, a flexible shaft having a distal end and a proximal end opposite said distal end, and a coupling mechanism that provides for the proximal end of the flexible shaft to securely attach to and detach from the handle.

Other objectives are achieved by providing a flexible endoscope having a coupling mechanism for releasably coupling a flexible shaft to a handle, wherein the coupling mechanism establishes an electrical interface/connection between the internal components of the shaft (e.g., imaging unit, illumination unit) and the internal components of the handle (e.g., power source, image controller, illumination controls, other drive electronics).

In some embodiments, the coupling mechanism provides an electrical interface, such as a electrical/power channel, for transferring power that comes from a power source disposed in the handle or is transmitted from an external source through the handle, to an illumination unit (light source) positioned in the flexible shaft. The electrical interface may further provide an additional channel, or utilize the same power channel, to enable illumination controls disposed in the handle to adjust the illumination unit. For example, the illumination controls may be adapted to change the intensity of the light source.

In other embodiments, the coupling mechanism provides an electrical interface between an imaging unit, and more specifically an image sensor, in the flexible shaft and an imaging controller in the handle. The imaging unit generates image data of the area in front of the distal end of the flexible shaft and sends the image data to the controller through a data channel established by the coupling mechanism. The controller processes the image data received via the data channel for subsequent display on a monitor or for transmission to an auxiliary or external device, such as a camera control unit (CCU). Further, the controller is adapted to control the imaging unit by sending electrical signals through the data channel to the imaging unit. As an example, the imaging controller may provide means for adjusting in real-time the image quality and characteristics of the image data. The electrical interface established by the coupling mechanism can transmit image data as an analog signal. Conversely, the image data can be transmitted through the coupling mechanism in digital format. The imaging controller may also be used to fine-tune the focus of the imaging unit or adjust the imaging unit to capture 2D or 3D images. The coupling mechanism further provides a power channel for supplying power from the handle to the imaging unit.

Additional objectives of the invention are achieved by providing a detachable shaft flexible endoscope having a handle, a flexible shaft, a coupling mechanism for releasably coupling the flexible shaft to the handle, wherein an illumination unit and an imaging unit are both disposed within the flexible shaft. In some embodiments, the illumination unit includes at least one light source positioned at the proximal end of the flexible shaft and a light-transmitting fiber bundle extending between the light source and the distal end of the flexible shaft, wherein the light-transmitting fiber bundle is adapted to pass light from the light source to the distal end of the flexible shaft. With the light source being disposed at the proximal end, power may be transmitted to thereto directly from the power channel provided by the coupling mechanism. Alternatively, a relatively short power cable may be connected between the power channel and the light source. In other embodiments, the illumination unit comprises a light source disposed at the distal end of the shaft and a power cable conducting electrical power from the power channel of the coupling mechanism to the light source. The illumination unit may further include heat-dissipating components to safely distribute heat generated by the light source throughout the flexible shaft. The light source may comprise a light emitting diode (LED). Other examples of the light source include light emitting electrochemical cells (LEEC), electroluminescent wires, organic light-emitting diodes (OLED), and polymer light-emitting diodes (PLED).

With regard to the imaging unit, in some embodiments, it comprises at least one electronic image sensor positioned substantially adjacent to an objective lens/window at the distal end of the flexible shaft. The image sensor receives power from the power channel of the coupling mechanism by means of a power cable extending therebetween. The power cable used to supply electricity to the light source may also be used to provide electricity to the image sensor. Alternatively, separate power cables may be used to supply power to the light source and the image sensor. In other embodiments, the imaging unit has at least one electronic image sensor positioned at the proximal end of the flexible shaft and an image-transmitting fiber bundle extending between the image sensor and an objective window disposed at the distal tip of the flexible shaft. The bundle, therefore, is adapted to pass an image detected at the objective window to an input of the image sensor. In some embodiments, the imaging unit includes a plurality of image sensors disposed either at the distal end of the flexible shaft or at the proximal end. The image sensor incorporated in the flexible shaft may be a Charged Coupled Device (CCD), a Complementary Metal-Oxide Semiconductor (CMOS) device, or any other solid-state imager.

The detachable shaft flexible endoscope may have an articulation unit for deflecting a distal portion of the flexible shaft and thus controlling the orientation of the distal tip of the shaft. For example, the distal portion of the flexible shaft can be deflected in any direction (e.g., up, down, left, right, etc.) by a degree of curvature between 0 degrees and at least 285 degrees relative to a longitudinal axis of the flexible shaft (in non-articulated state). Similar to the imaging unit and the illumination unit, the articulation unit is disposed within the flexible shaft. A steering control, i.e., controller or control mechanism for the articulation unit, is also configured on the flexible shaft. The steering control is adapted to control the direction and extent of the bending movement of the distal portion of the flexible shaft. Accordingly, all the components related to the articulation/deflection capabilities of the endoscope, i.e., the articulation unit and steering control, are arranged in/on the flexible shaft.

The articulation unit may comprise at least one tension wire that is coupled to the distal end of the flexible shaft and extends to the steering control. In some embodiments, a plurality of tension wires may be used in the articulation unit, providing increased precision and accuracy in the deflection of the distal portion of the flexible shaft. By movement or manipulation of the steering control, a tension (e.g., pushing, pulling) is applied directly to the at least one tension wire, which subsequently produces a bending motion in the distal portion of the shaft. In other embodiments, the articulation unit may comprise an actuator disposed in the shaft and connected between the steering control and the at least one tension wire. When the steering control is moved or manipulated, a steering signal representing a tensile force and a direction of deflection is sent to the actuator. The actuator then applies a tension to the tension wire based on the signal. The amount and direction in which the distal portion of the shaft bends is correlated to the applied tensile force. With either configuration, the articulation unit is capable of precisely deflecting the flexible shaft in small increments.

The tension wire disposed in the flexible shaft may comprise any material sufficient to produce the range of motion of the distal portion of the flexible shaft. For example, the tension wire may be a mechanical wire. Alternatively, the tension wire can be a solid rod or a chain.

The shape of the detachable shaft flexible endoscope when the shaft and the handle are coupled together is substantially linear in some embodiments. In other embodiments, the detachable shaft flexible endoscope has a pistol-style shape, wherein the handle provides an ergonomic grip for holding in a user's (medical practitioner, surgeon) hand. The pistol shape further accommodates a design feature where the illumination unit, imaging unit, articulation unit, and steering control are all disposed in/on the flexible shaft. The pistol style handle provides for the steering control (e.g., finger lever, trigger) to be positioned within reach of the index finger or middle finger of the user's hand.

With delicate components of the instrument being located within one section, i.e., the flexible shaft, and the handle having the robust drive electronics (e.g., imaging control unit, illumination control), this arrangement provides for easier means of locating and diagnosing problems/issues with the endoscope, repairing the instrument, and/or replacing parts of the instrument. More specifically, if the flexible endoscope has a problem with deflecting or providing sufficient illumination, it may be determined quickly that the issue resides in the shaft. The user can then easily detach the malfunctioning shaft, send it to the manufacturer for repair, and substitute/replace the malfunctioning shaft with a new one, without substantial downtime.

Additional objects of the invention are achieved by providing an endoscope including a handle, a flexible shaft, and a coupling mechanism for attaching the flexible shaft to the handle, the coupling mechanism having a first component disposed on the proximal end of the flexible shaft and a second component disposed on a distal end of the handle, wherein the first and second components are adapted to engage each other. The first and second components also independently seal the shaft and handle, respectively, from fluid leakage and contamination with germs, bacteria, or other biological materials. In particular, the first and second components are adapted to provide fluid-proof, static seals that prevent or reduce the likelihood of communication of fluid into the interior compartments of the flexible shaft and handle. The seals enable both parts of the endoscope to be reprocessed (i.e., cleaned, disinfected and sterilized) while in a detached configuration. Further, upon coupling the shaft to the handle, the first and second components collectively create a seal therebetween to prevent any contamination of the interior compartments as well as the coupling mechanism itself.

In some embodiments, the detachable shaft flexible endoscope further comprises at least one leak check valve or port disposed on the flexible shaft. The leak check valve functions as a means for verifying that no foreign fluids enter into the interior of the flexible shaft. The leak check valve can be configured in an open state so that any fluid that may have entered inside the flexible shaft can be drained or discharged. Further, in some embodiments, the leak check valve is adapted to receive a tube connected to a suction or pump unit for evacuating any fluids that may have leaked into the interior of the flexible shaft. When the leak check valve is configured in a closed state, the valve forms an air-tight and pressure-tight seal.

Further objects of the present invention are achieved by providing a detachable shaft flexible endoscopic instrument comprising a flexible shaft having a distal end and a proximal and a coupling mechanism adapted to releasably attach one of a plurality of handles to the proximal end of the shaft. Each handle has different characteristics and provides different functions when coupled to the flexible shaft. For example, a first handle may comprise drive electronics for the imaging unit and the illumination unit as well as a external cable that is adapted to plug into a CCU. Instead of a cable, a second handle may comprise an internal battery and a wireless transmitter-receiver for communicating with the CCU. A third handle may comprise an internal battery and an integrated monitor for displaying the image detected by the imaging unit in the flexible shaft. Conversely, a fourth handle may comprise an external cable (i.e., USB) that is adapted to plug into a computer, such as a personal computer, laptop, tablet, iPad, or other processing device.

Other objects of the invention and its particular features and advantages will become more apparent from consideration of the following drawings and accompanying detailed description. It should be understood that the detailed description and specific examples, while indicating the preferred embodiment of the invention, are intended for purposes of illustration only and are not intended to limit the scope of the invention.

DETAILED DESCRIPTION OF THE INVENTION

The following detailed description illustrates the invention by way of example, not by way of limitation of the principles of the invention. This description will enable one skilled in the art to make and use the invention, and describes several embodiments, adaptations, variations, alternatives and uses of the invention, including what is presently believed to be the best mode of carrying out the invention.

Figure 1:
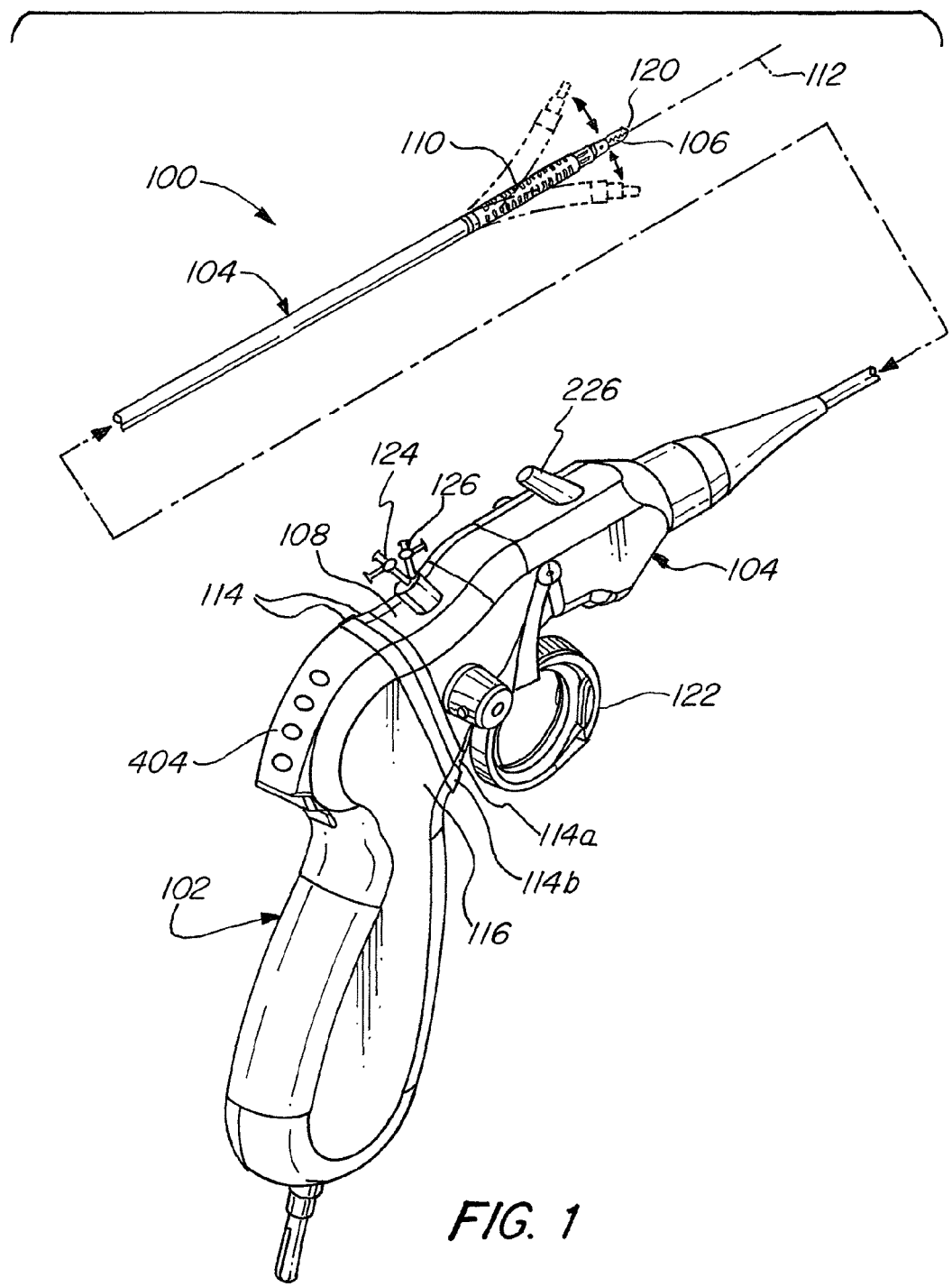
FIG. 1 is a perspective view of a detachable shaft flexible endoscope according to an exemplary embodiment of the present invention.
Figure 2:
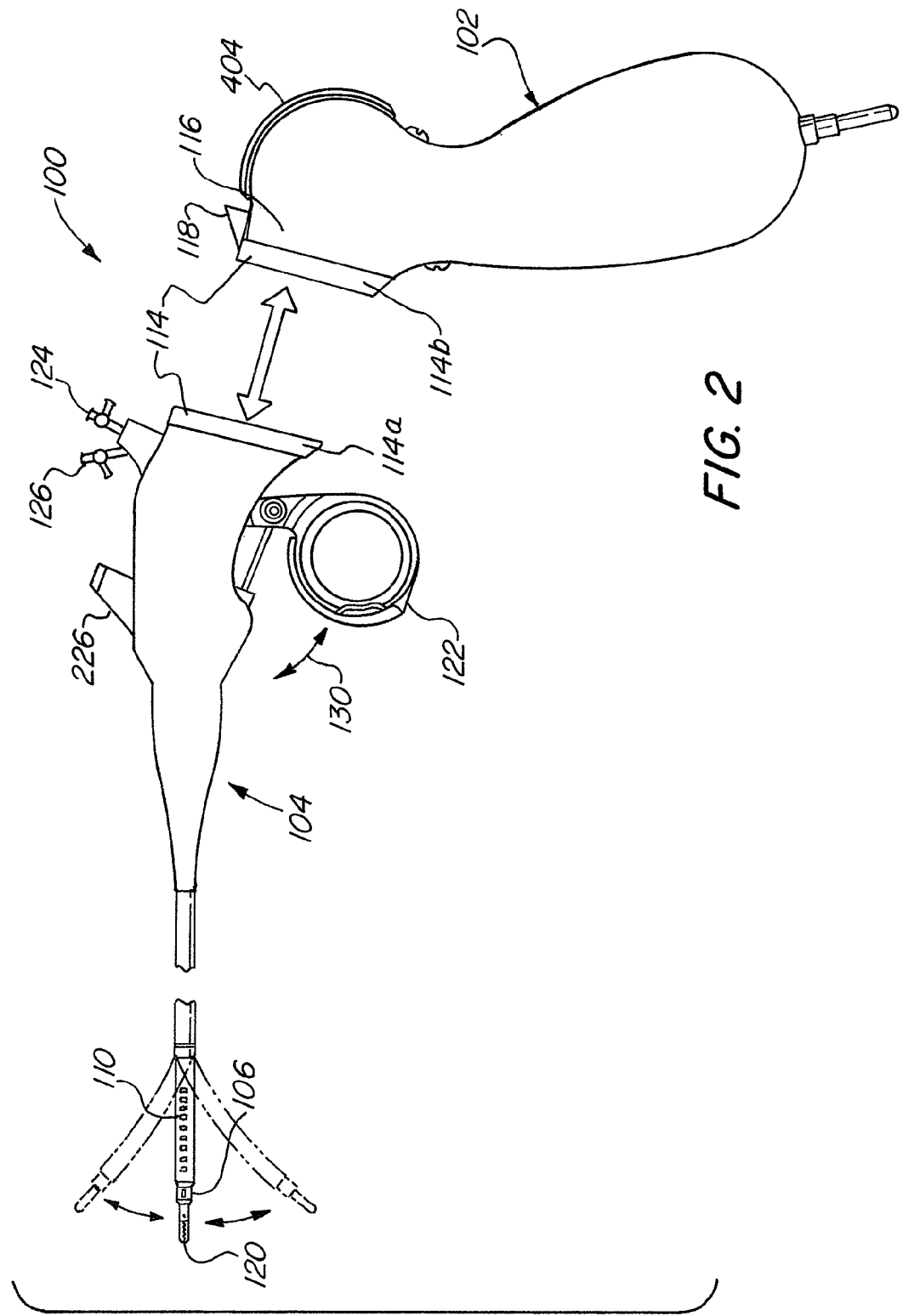
FIG. 2 is a side view of the detachable shaft flexible endoscope of FIG. 1.

Referring to the figures in detail and first to FIGS. 1-2, there is shown a flexible endoscope 100 according to an exemplary embodiment of the present invention. The flexible endoscope 100 includes a handle 102 and a flexible shaft 104. The flexible shaft 104 has a distal end 106 and a proximal end 108, wherein the flexible shaft 104 is adapted to be inserted into a cavity of a living body ("operative site"). A distal portion (or bending portion) 110 disposed proximally from the distal end 106 can be articulated and deflected in any direction within a plane relative to a longitudinal axis 112, which is defined by the flexible shaft 104. Accordingly, the orientation of the distal end 106 can be adjusted by a medical practitioner, e.g., surgeon, using the endoscope ("user"). The distal end 106 and proximal end 108, however, are substantially rigid relative to the distal portion 110 of the flexible shaft 104. The handle 102 of the endoscope 100 is ergonomically designed for comfortable use by the user. The handle 102 is designed so that the user can easily operate the endoscope 100 using one hand.

In some embodiments, the endoscope 100—flexible shaft 104 combined with the handle 102—has a pistol-style shape, wherein the handle 102 resembles a pistol grip. The pistol-style shape provides the user a comfortable and easy way of holding the endoscope while operating and controlling its multiple functions. Further, the pistol-style shape provides a structure in which the internal components of the endoscope may be advantageously positioned in or on the flexible shaft and handle. In other embodiments, the endoscope 100 may have a substantially linear shape, wherein the ergonomic handle is aligned with the flexible shaft.

The endoscope 100 also has a coupling mechanism 114 which releasably attaches and detaches the flexible shaft 104 to the handle 102. More specifically, the coupling mechanism 114 can be formed with two components, a first component 114a disposed on the proximal end 108 of the flexible shaft 104 and a second component 114b disposed on a distal end 116 of the handle 102. The first component 114a is adapted either as a female or male connector while the second component 114b is adapted as a male or female connector, respectively. When the first component 114a is inserted into the second component 114b, the flexible shaft 104 is coupled to the handle 102 and thus the flexible shaft 104 becomes operable with the handle 102. The coupling mechanism 114 provides an electrical interface which connects the internal components of the flexible shaft 104 with the internal components of the handle 102. The coupling mechanism 114 further includes a lock 118 to ensure that the flexible shaft 104 and the handle 102 are securely attached to each other. Accordingly, the flexible shaft 104 cannot be inadvertently detached from the handle 102.

Figure 3A:
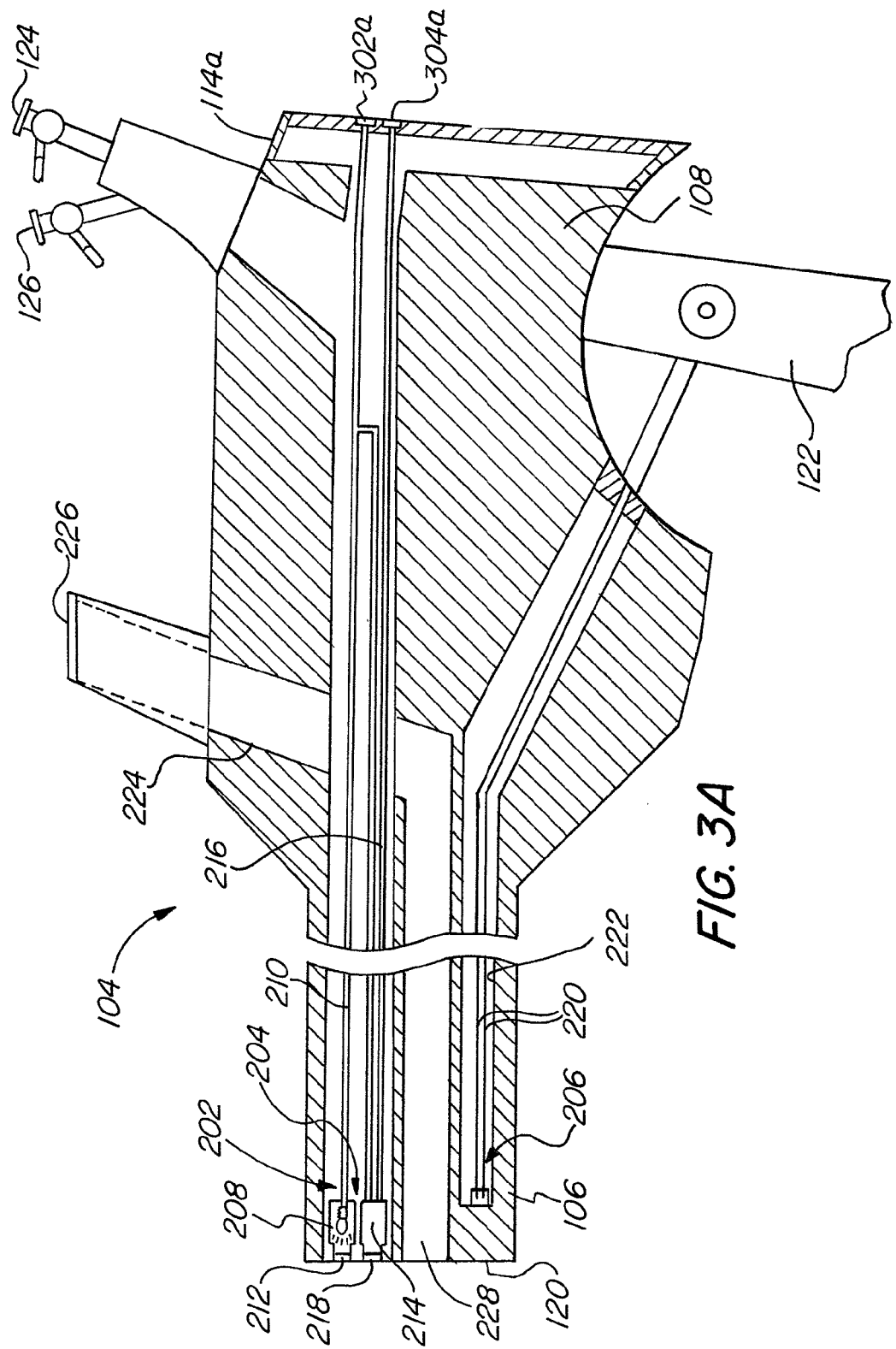
FIG. 3A is a detailed view of the inside of the detachable shaft flexible endoscope of FIG. 1 having a flexible shaft according to one embodiment.

FIG. 3A shows a detailed view of the interior of the flexible shaft 104 of endoscope 100 according to one embodiment. Incorporated within the flexible shaft 104 is at least one illumination unit 202 and at least one imaging unit 204. Both the illumination unit 202 and the imaging unit 204 extend the length of the flexible shaft 104, from the distal end 106 to the first component 114a of the coupling mechanism 114 at the proximal end 108. The illumination unit 202 comprises a light source 208 disposed at the distal end 106 and a power cable 210 connected to the light source 208 for providing electrical power to the light source 208. In some embodiments, the light source 208 is a light emitting diode (LED), such as organic light emitting diodes, polymer light emitting diodes, and solid-state lighting. Other examples of lights sources that may be used in the endoscope include light emitting electrochemical cells (LEEC) and electroluminescent wires. The light source 208 is further mounted substantially adjacent to a window 212 at a distal tip 120 of the distal end 106. Upon receiving electrical power, the light source 208 shines light through the window 212 to an area in front of the distal end 106 of the flexible shaft 104.

The imaging unit 204, as shown in FIG. 3A, comprises an image sensor 214 mounted at the distal end 106 and substantially adjacent to an objective lens 218 at the distal tip 120. In one embodiment, the image sensor is a solid state image sensor. For example, the image sensor 214 may be implemented as a charge-coupled device (CCD), a complementary symmetry metal-oxide semiconductor (CMOS) active pixel image sensor, a camera or any other commercially available imaging device. When the image sensor 214 receives power from the power cable 210, it operates to capture an image of the area in front of the distal end 106 of the flexible shaft 104, i.e. operative site. More specifically, the objective lens 218 directs the image towards the image sensor 214. The image sensor 214, in turn, converts the image into image data. In one embodiment, the image sensor 214 generates the image data in analog form, whereas in another embodiment, it generates image data in digital form. The imaging unit 204 further comprises an image-transmitting cable 216 for transmitting the image data from the image sensor 214 to the coupling mechanism 114 and thereafter to an imaging controller in the handle 102.

The flexible shaft 104 can also be equipped with an articulation unit 206 for bending/deflecting the distal portion 110 of the flexible shaft 104. The articulation unit 206 extends within the shaft between the distal end 106 to a steering control 122 positioned on the shaft proximate to the proximal end 108. The articulation unit 206, as shown in FIG. 3A, comprises at least one tension wire 220 passing through a lumen 222. The tension wire 220 comprises a mechanical wire in some embodiments. In other embodiments, the tension wire 220 comprises a solid rod or a chain. One end of the tension wire 220 is embedded in the distal end 106 while an opposite end of the tension wire 220 is operably connected to the steering control 122. By adjusting the tension in the at least one tension wire 220 via the steering control 122, the bending portion 110 of the flexible shaft 104 can be articulated away from the longitudinal axis 112. The articulation unit 206, therefore, can deflect the distal end 106 to adjust the orientation of the distal tip 120. As such, the operative site where the image sensor and the light source are focused may be changed without having to shift the entire endoscopic instrument and more specifically the handle 102. The articulation unit 206 can deflect the distal end 106 in any direction (360 degrees) with respect to the longitudinal axis 112 of the shaft. For example, the distal end can deflect up or down, left or right, or any combination of the relative directions. Further, the distal portion 110 can be deflected by a degree of curvature between 0 degrees and at least 285 degrees relative to the longitudinal axis 112.

The detachable shaft flexible endoscope 100 can further include a working channel 224. The structure of the working channel 224 is defined by a central lumen disposed within the flexible shaft 104, as illustrated in FIG. 3A. The working channel 224 has an inlet port 226 disposed substantially at the proximal end 108 of the flexible shaft 104 and an outlet port 228 at the distal tip 120. The inlet port 226 is integrated with the exterior surface of the flexible shaft 104 and provides access to the working channel 224. The purpose of the working channel is to provide passage for fluids and/or medical instruments into the body cavity. In particular, fluids or medical instruments can be inserted into the working channel 224 through the inlet port 226 and guided towards and out of the outlet port 228.

Figure 3B:
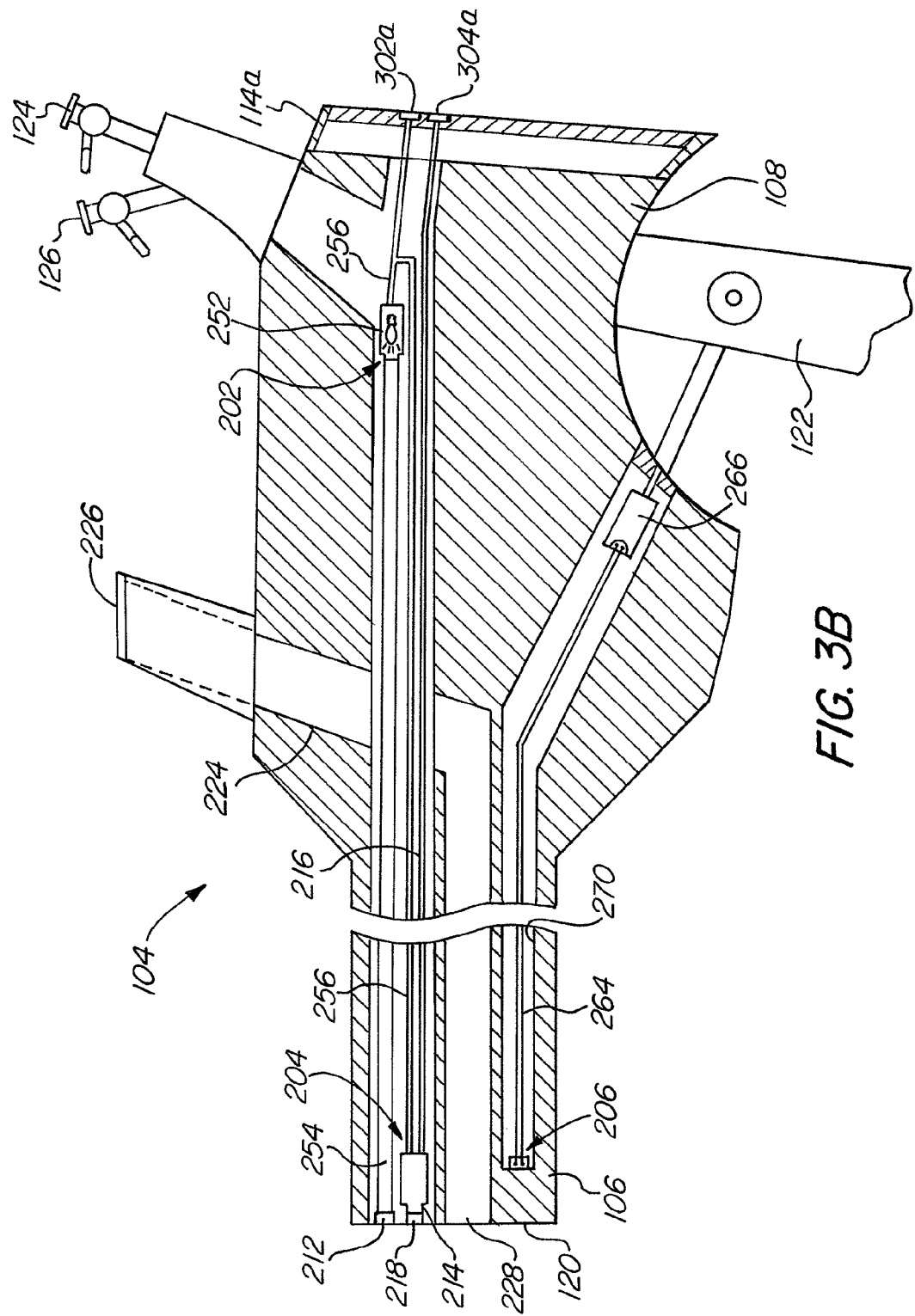
FIG. 3B is a detailed view of the inside of the detachable shaft flexible endoscope of FIG. 1 having a flexible shaft according to another embodiment.

FIG. 3B shows another embodiment of the flexible shaft 104. In this configuration, the flexible shaft 104 comprises an illumination unit 202 and imaging unit 204 extending the length of the flexible shaft 104, between the distal tip 120 and the proximal end 108 as well as an articulation unit 206 connected between the distal end 106 and a steering control 122 positioned proximate to the proximal end 108. The illumination unit 202 comprises a light source 252, such as a LED, disposed at the proximal end 108 of the flexible shaft 104, and power cable 256 connected to the light source 252 for providing electrical power thereto. Since the light source 252 is located away from the distal tip 120 of the shaft 104, a light-transmitting fiber bundle 254 is used to conduct light from the light source 252 to the window 212.

The imaging unit 204, as shown in FIG. 3B, may have the same distal configuration as the imaging unit 204 shown in FIG. 3A. In particular, the imaging unit 204 has an image sensor 214 positioned substantially adjacent to the objective lens 218 at the distal end 106 of the shaft. Alternatively, the imaging unit 204 may have a proximal configuration. Specifically, the image sensor may be disposed at or proximate to the proximal end 108. In order to convey an image from the objective lens 218 to the proximal image sensor, an image-transmitting fiber bundle is connected therebetween. An image of the operative site is directed into the image-transmitting fiber bundle, which then transmits the optical image to the image sensor. The image sensor subsequently captures the image and converts it into image data, either in analog or digital signal form. An image-transmitting cable 216 disposed in the flexible shaft 104 is used to transmit the image data from the proximal image sensor to the coupling mechanism 114.

As shown in FIG. 3B, the articulation unit 206 may comprise at least one tension wire 264 (e.g., mechanical wire, solid rod, chain) and an actuator 266. The tension wire 264 is positioned within a lumen 270 and has a first end embedded in the distal end 106 of the flexible shaft 104 and a second end connected to the actuator 266. The actuator 266 is adapted to adjust the tension in the tension wire 264, thereby deflecting the distal portion 110 of the flexible shaft 104. The actuator 266 may comprise a piezoelectric motor in some embodiments. The actuator 266 is in operable connection with the steering control 122 located near the proximal end 108 of the shaft. A steering signal for controlling the deflection of the distal portion is generated by moving the steering control 122. The steering signal is subsequently transmitted from the steering control 122 to the actuator 266, wherein the steering signal establishes the amount of tension the actuator 266 must apply to the tension wire 264. As a result, the bending portion 110 of the shaft articulates in a plane relative to the longitudinal axis 112.

In some embodiments, the steering control 122 comprises at least one lever member or pistol trigger for controlling the articulation of the distal portion 110. The steering control also includes a ring portion for receiving the index or middle finger of the user. The lever arm moves in a single plane, indicated by the arrow 130. Such single plane movement of the lever arm corresponds to a movement of the distal portion 110. With the steering control 122 being disposed proximate to the proximal end 108, the user can readily access the steering control 122 with his or her index or middle finger, while still being able to maintain his or her grip on the handle 102 and to access other control buttons 404 (discussed further below) positioned on the handle 102. It is therefore very simple to actuate the distal portion 110 of the shaft and adjust the illumination unit and/or imaging unit via buttons 404 simultaneously. It is noted that the flexible shaft 104 may be equipped with two levers in order to articulate the distal portion 110 in multiple planes.

Although two embodiment of the flexible shaft 104 are disclosed above and shown in FIGS. 3A-3B, other flexible shafts having different variations can be used with the detachable shaft flexible endoscope 100. Furthermore, the flexible shaft 104 can incorporate more than one illumination unit and/or imaging unit. For example, the flexible shaft 104 can have two imaging units 204 capturing an image through two objective lenses 218 at the distal tip 120. With two imaging units, the image data from both image sensors can be used to create a three-dimensional stereoscopic image for display. The flexible shaft 104 can also have two or more illumination units 202 to provide increased lighting through the windows 212 to the area in front of the distal end of the shaft. The two or more illumination units 202 may also be used to provide different forms of illumination. For example, the illumination units can differ in terms of their color spectrum. The illumination units may differ in terms of their light source type, e.g., LEDs, LEEC, electroluminescent wires, OLEDs, and PLEDs. Also, the articulation unit 206 may comprise multiple tension wires 220 to provide for deflection of the distal portion 110 of the flexible shaft 104.

Figure 4A:
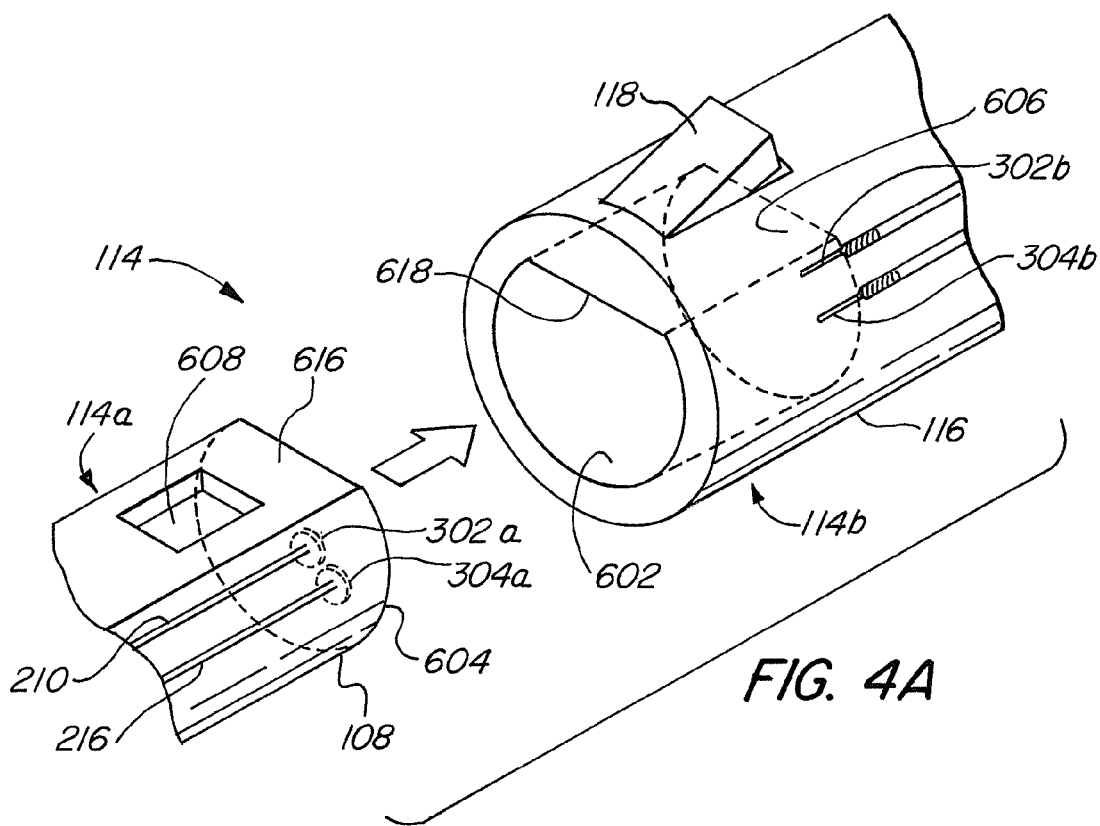
FIG. 4A is a perspective view of one embodiment of the coupling mechanism of the detachable shaft flexible endoscope of FIG. 1.
Figure 4B:
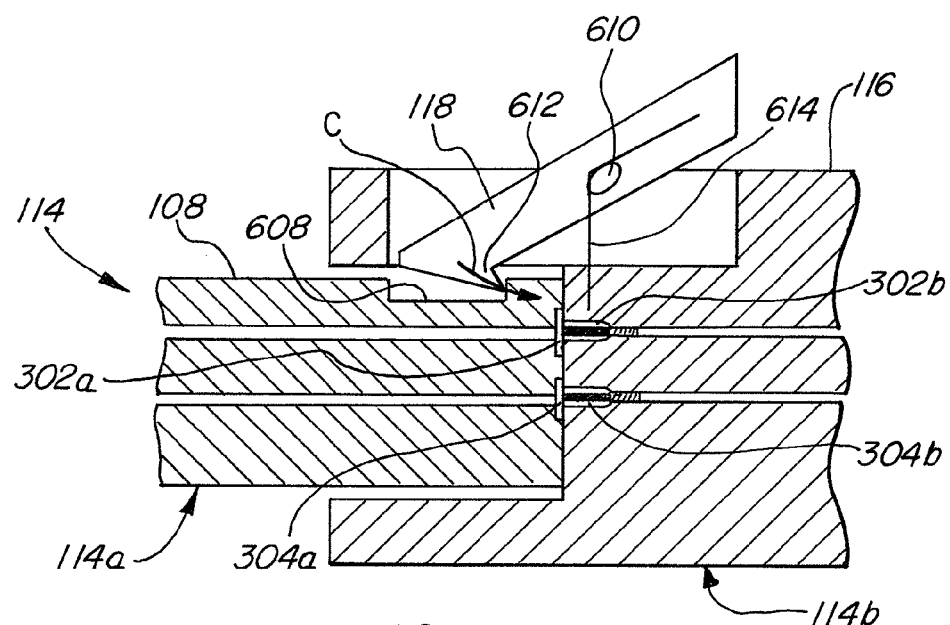
FIG. 4B is a detailed view of one embodiment of the coupling mechanism of the detachable shaft flexible endoscope of FIG. 1.

FIGS. 4A-4B show one example of the coupling mechanism 114. A first component 114a ("male component") and a second component 114b ("female component"), wherein the first component is adapted to engage or insert into the second component. A locking mechanism 118 is also provided, wherein after the first and second components are mated with each other, the lock—upon engagement/activation—establishes a secure attachment therebetween. As shown in FIG. 4A, the first component 114a is disposed on the proximal end 108 of the shaft 104 while the second component 114b is disposed on the distal end 116 of the handle 102. However, in other embodiments of the endoscope, the components may be positioned in opposite manner, such that the first component is located on the distal end of the handle and the second component is located on the proximal end of the shaft.

In some embodiments, the first component 114a of the coupling mechanism may comprise merely a portion of the distal end 108 of the flexible shaft 104 (FIGS. 4A-4B). The first component 114a can be shaped such that its cross section is partially non-circular. As shown in FIG. 4A, the cross section of the first component 114a can have a semicircular shape with a flat side 616. The second component 114b comprises a recess 602 formed on the distal end 116 of the handle 102. The recess 602 is designed with a preset depth such that upon mating the two components, the proximal end face 604 of the shaft 104 contacts the distal end face 606 of the handle 102. In addition, the recess 602 has a cross-sectional shape which corresponds to the non-circular cross section of the first component 114a. With the first and second components having complimentary non-circular cross-sectional profiles, a fitted arrangement is created therebetween. Moreover, there is only one way to mate the first component with the second component. This ensures that the flexible shaft 104 is properly oriented and engaged with the handle 102.

The lock 118 may comprise a lever disposed on the distal end 116 of the handle 102 and an aperture 608 that is formed in the flat side 616 of the first component 114a. The lever of lock mechanism 118 is pivotably mounted to the outer surface of the distal end 116, by way of a support shaft 610, so as to oppose the flat side 618 of the recess 602. As illustrated in FIG. 4B, a hook 612 is disposed at the distal end of the lever and inwardly projected from the flat side 618 of the recess 602. Further, a coil spring 614 is attached to the shaft 610 in order to pivotably force the lever in a direction C. Once the first component 114a is mated with the second component 114b (e.g., first component inserted within the recess 602 of the second component), the hook 612 latches onto/within the aperture 608 by force of the coil spring 614. The proximal end face 604 is fixed to and placed in pressing contact with the distal end face 606 due to the hook 612 being lodged within the aperture 608. Accordingly, a secure attachment is automatically achieved between the flexible shaft 104 and the handle 102 once the first and second components 114a, 114b are fully mated to each other.

In order to detach the shaft 104 from the handle 102, the user merely unlocks the locking mechanism 118 (e.g., pivot the lever of lock 118 so that the hook 612 no longer latches to aperture 608) and withdraw the first component 114a from within the recess 602 of the second component 114b.

In addition to providing the means for releasably attaching the handle to the shaft, the coupling mechanism 114 is adapted to provide seals to inhibit fluid communication into the interiors of the handle and the shaft and thus reduce the likelihood of contamination of internal components (e.g., illumination unit, imaging unit, drive electronics). In particular, the first component 114a forms a first seal along the proximal end face 604 to prevent the ingress of foreign fluid into the shaft. Similarly, the second component 114b independently forms a second seal on the distal end face 606, thereby preventing the ingress of foreign fluid into the handle 102. When the endoscope 100 is in a detached configuration, the first and second components 114a, 114b maintain a sealed enclosure for the interiors of the handle and the shaft. The internal components within the handle 102 and shaft 104 are substantially protected from fluid contact, which reduces the likelihood that they will be susceptible to damage. Moreover, the seals of the first and second components prevent any contamination of the interiors of the handle and shaft with germs, bacteria, and other biological material. Since the articulation unit and steering control are positioned on the flexible shaft, the coupling mechanism does not need to provide an interface adapted for mechanical movement and thus the first and second components may provide static seals.

When the first and second components 114a, 114b are mated to each other, an external seal is created along the coupling mechanism between the shaft and handle. Specifically, the first and second components may be adapted with additional features, e.g., protrusions, projections, rubber washers, to reduce the likelihood that foreign fluid is communicated into a region between the shaft and handle within the coupling mechanism 114. The external seal similarly reduces the likelihood that the interiors of the handle and shaft will be exposed to foreign fluid and other contaminants.

It is noted that the above embodiment of the coupling mechanism is merely exemplary, and the present invention is not limited to this particular coupling mechanism. The detachable shaft flexible endoscope according to the present invention can incorporate other coupling mechanisms which provide a secure, sealed attachment between the flexible shaft 104 and the handle 102. For example, a coupling mechanism using magnetic fastening means can be used to securely attach the flexible shaft 104 to the handle 102.

To further ensure that foreign fluid does not enter and reside inside the interior portions of the endoscope and damage delicate components contained therein, i.e. illumination unit, imaging unit, and articulation unit, the endoscope 100 is equipped with a check valve 124 mounted to the flexible shaft 104 (FIGS. 1-2). The check valve 124 is adapted to indicate a presence of fluid in the interior of the shaft 104 as well as discharge any fluid that may have entered into the shaft. By positioning all the delicate components within the shaft, only one check valve is required. On the other hand, the handle 102 contains more robust elements, such as drive electronics for controlling the illumination unit and the imaging unit, and therefore does not require a check valve. The check valve 124 is communicatively connected to the interior of the shaft 104 containing the illumination unit 202 and the imaging unit 204. If the check valve lever is configured in the open position, the check valve 124 is placed in communicative connection with the outside, i.e., outside environment. The check valve may then be used to remove any fluid that may be present in the shaft interior. In some embodiments, the check valve 124 may be adapted to connect to a pump or suction unit for evacuating the interior of the shaft of any and all fluids present therein. Conversely, if the check valve lever is closed, the connection to the interior of the shaft is restricted.

In some embodiments, the check valve 124 may further incorporate a vent valve 126, which provides an opening for the release of gas-based fluids contained within the interior of the shaft and for adjusting the pressure inside the interior of the shaft (FIGS. 1-2). When the pressure inside the shaft substantially matches the pressure of the outside environment, the vent valve 126 may be closed. In some embodiments, the vent valve 126 may be used to perform a leak test, wherein an air supply unit is connected thereto to feed air into the shaft interior.

Still referring to FIGS. 4A-4B, the coupling mechanism 114 creates interface connections between the internal components of the flexible shaft 104 and the handle 102. In particular, the coupling mechanism 114 provides at least one electrical interface for each the illumination unit 202 and the imaging unit 204. Since the articulation unit 206 and the steering control 122 are located in the shaft, no dynamic mechanical interfaces are required. The coupling mechanism 114 establishes a power channel 302 for conducting electrical power from the handle 102 to the power cable 210 (or 256) in the flexible shaft 104. The power channel 302 comprises a pin 302b disposed on the distal end face 606 of the handle and a contact region 302a disposed on the proximal end face 604 of the flexible shaft. The pin 302b and the contact region 302a are aligned longitudinally and radially in a matching pattern so that when the first and second components 114a, 114b are mated, the pin 302b contacts the corresponding contact region 302a. Accordingly, by engaging the first component with the second component, the pin 302b is positioned in matching arrangement with the contact region 302a. No additional adjustment is required in order to properly establish physical and electrical contact between the pin and contact region.

A data channel 304 is further provided by the coupling mechanism 114. The data channel 304 is created by a pin 304b making contact with a contact region 304a. The pin 304b is electrically connected to an image-transmitting cable 428, which in turn is connected to an imaging controller 402 (discussed further below) inside the handle. The contact pad 304a is electrically connected to the image-transmitting cable 216 in the flexible shaft 104. Once the data channel 304 is established, it transmits image data from the image sensor 214 to the controller 402 (FIG. 5), wherein the image data is processed.

In some embodiments, the power channel 302 and the data channel 304 may comprise a pogo pin or spring-loaded pin and a contact pad. The pogo pins are embedded in the distal end face 606 of the handle 102 while the contact pads 302a are positioned on the proximal end 604 in axial alignment with the pogo pins. When the first component 114a and the second component 114b are mated, the pogo pins maintain constant contact with the contact pads. Furthermore, the contact pads can be adapted to have a wider surface area than the tip of the pogo pins to account for potential deviations in alignment. This ensured that proper contact is made between the pins and pads. In other embodiments, conventional electrical pins and contact housings (e.g., sockets) may be used to create the electrical connections of the coupling mechanism.

Figure 5:
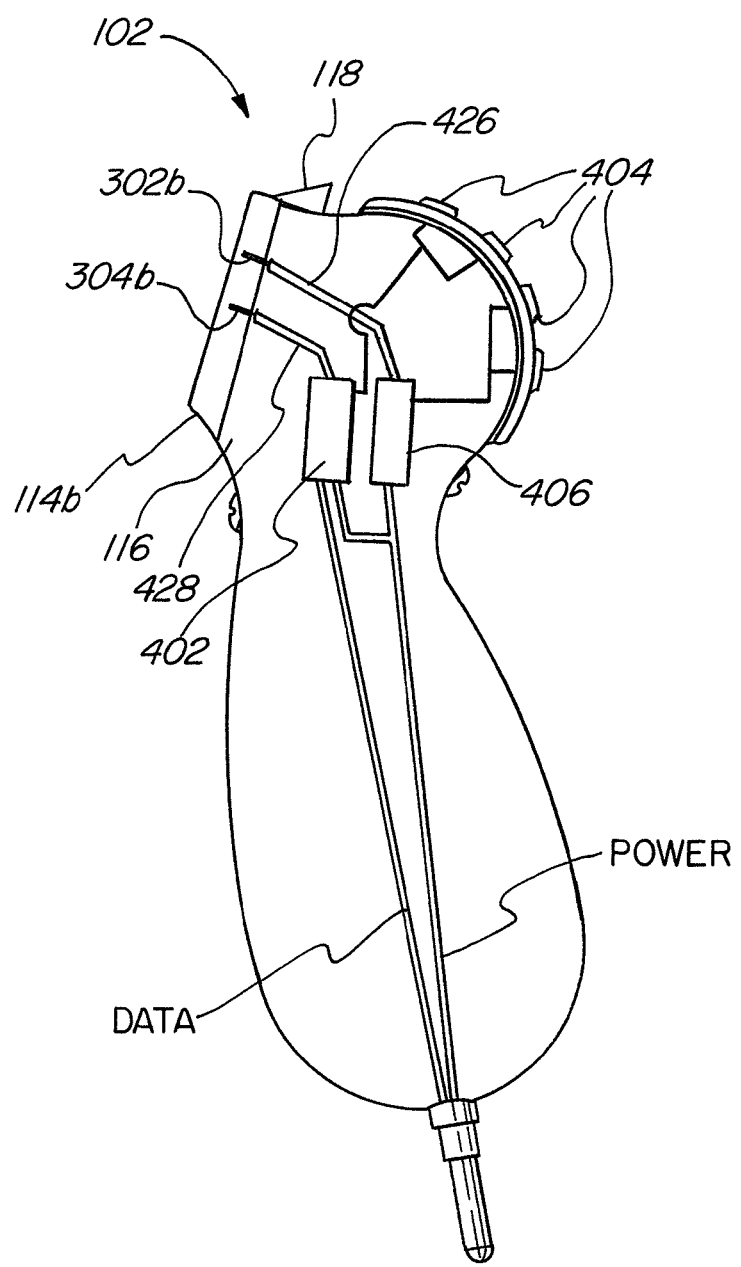
FIG. 5 is a detailed view of one embodiment of the handle of the detachable shaft flexible endoscope of FIG. 1.

Referring to FIG. 5, the handle 102 of the detachable shaft flexible endoscope 100 is shown. The handle 102 includes the drive electronics for the controlling the illumination unit 202 and the imaging unit 204. Specifically, an image controller 402 is disposed within the handle 102, wherein the controller 402 is adapted to process and convert the image data received via the data channel of the coupling mechanism 114 into a format suitable for transmission and display on a monitor. The controller 402 can encode/decode the image data as well as adjust the image data to alter how the image is displayed on a display unit. Using a control pad 404 mounted on the exterior of the handle 102 and connected to the imaging controller 402, a user can adjust the image quality of the image data, such as increasing or decreasing the resolution (e.g., pixel resolution, spatial resolution, spectral resolution, temporal resolution). Where the imaging unit 204 comprises two or more image sensors, the controller 402 may be adapted to adjust the image quality between 2D display and 3D display. Alternatively, the image controller 402 has the capability to perform stereoscopy or 3D imaging to provide depth in the image data. The controller 402 can also transmit a signal to the image sensor 214 to adjust various settings of the sensor. For example, a control signal can be sent to the image sensor to zoom in or zoom out on the operative site. Through the control pad 404 and controller 402, the user may be able to adjust the focus of the image sensor and improve the clarity of the image data received by the controller.

An illumination control unit 406 connected to the control pad 404 can also be incorporated within the handle 102, wherein the illumination control 406 adjusts the light source 208 (or 252). For example, the illumination control 406 can function to turn on or off the light source. Further, the intensity of the light projected from the light source can be increased or decreased by the user via the control pad 404 and illumination control 406. Where the endoscope 100 includes more than one type of light source, the user can adjust which type of lighting to use at any given moment.

The handle 102 also includes a power cable 426 to provide electrical power to the illumination unit 202 and the imaging unit 204 via the electrical channel 302 of the coupling mechanism. In some embodiments, the power cable 426 receives electrical power from an internal battery source disposed in the handle 102. Alternatively, the power cable 426 feed electrical power to internal components of the shaft from an external power source, which is connected to the handle 102.

It should be noted that the control pad 404 can include a battery status indicator, which displays whether the endoscope 100 is being powered by an external source or by an internal battery, and shows battery life.

Figure 6:
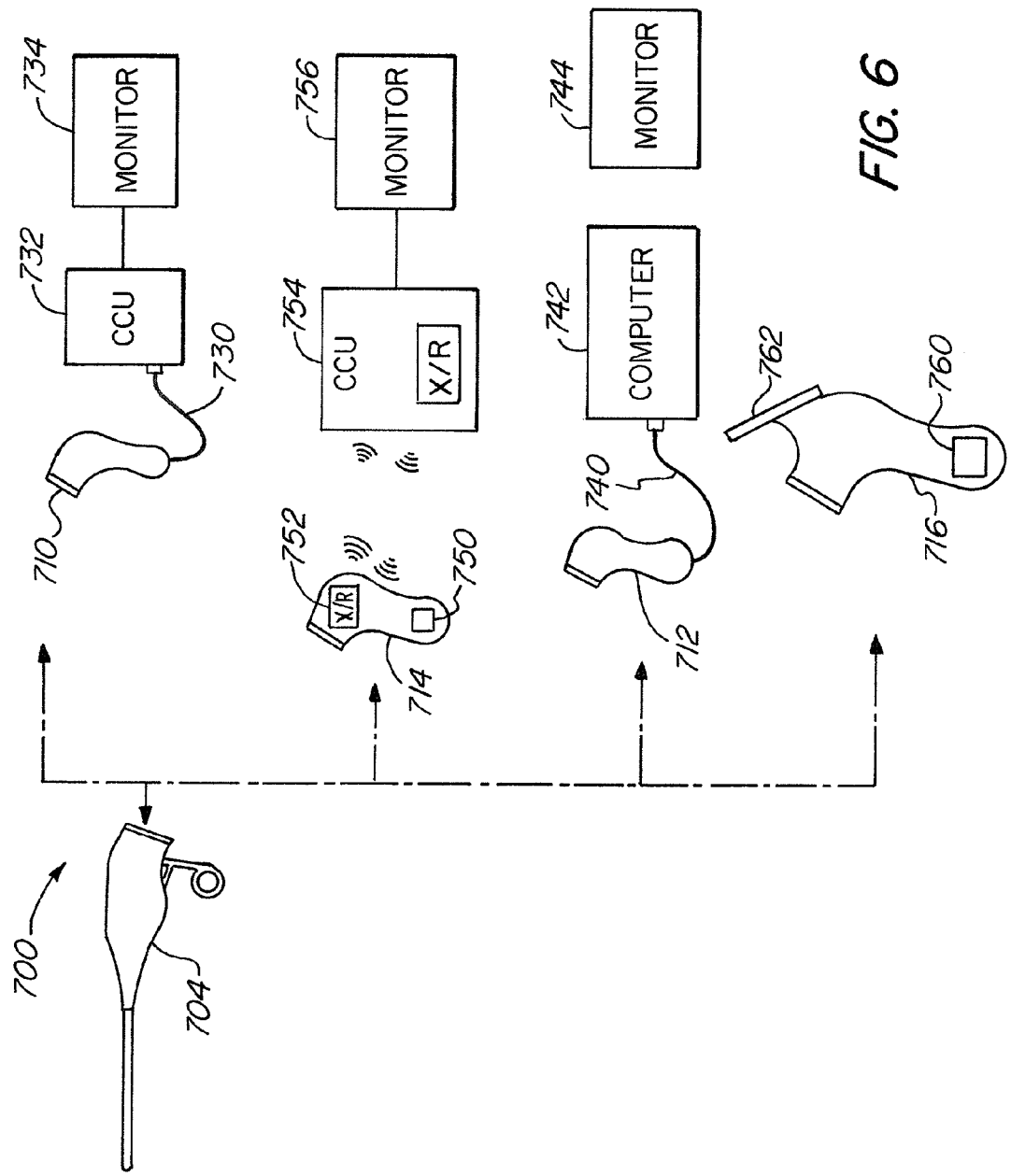
FIG. 6 is a side view of a detachable shaft flexible endoscope according to an exemplary embodiment of the present invention.

FIG. 6 shows another embodiment of the detachable shaft flexible endoscope, and more specifically, a flexible endoscope system 700. The endoscope system 700 comprises a flexible shaft 704 having a distal end and a proximal end. An illumination unit and imaging unit are both disposed within the flexible shaft. Further, the shaft 704 includes an articulation unit which articulates a distal portion of the shaft 704 when a steering control is moved. The shaft 704 may also comprise a check valve that is adapted to indicate/detect and discharge any fluid that may have entered into an interior of the shaft. The endoscope 700 also comprises a coupling mechanism 714 for releasably attaching the proximal end 708 of the shaft to one of a plurality of handles 710, 712, 714, 716, wherein the handles each have different capabilities and functions. For instance, handles 710, 712 each have the same configuration of handle 102 (FIG. 5) and further have external cables 730, 740 that are adapted to plug into auxiliary devices 732, 742, respectively. The external cables 730, 740 provide the means for the handles 710, 712 to communicate image data received from the imaging unit to the auxiliary devices. The auxiliary devices are adapted to then process and manipulate the image data for display on a monitor 734, 744. The auxiliary devices may also perform image optimization as well as record/save the image data. The external cable also transmits electrical power supplied by the auxiliary device to the handle and the shaft. With regard to handle 710, the external cable 730 connects to a camera control unit (CCU) 732, which displays the image data on the monitor 734. In some embodiments, the CCU 732 is adapted to drive the imaging unit and control various parameters thereof to adjust the quality of the image data. The external cable 740 of handle 712, on the other hand, can connect to a computer 742, such as a desktop, laptop, netbook, tablet, and iPad. Similar to the CCU 732, the computer 742 is adapted to receive and process image data and send the resulting image to a monitor 744.

The handle 714 comprises an internal battery pack 750 to provide electrical power to the drive electronics present in the handle and the internal components of the shaft. Further, a transmitter-receiver unit 752 is integrated with the handle 714, providing wireless communication between the endoscope 700 and an auxiliary device 754. As shown in FIG. 6, the transmitter-receiver unit 752 wirelessly transmits image data to a CCU 754 for display on a monitor 756 and may receive control signals from the CCU. Examples of wireless technology used by the transmitter-receiver unit include radio frequency communication, infrared short-range communication, Bluetooth, and ultra-wideband communication.

The handle 716 differs from the other handles because it includes an internal battery source 760 and has an auxiliary device 762 directly integrated therein. As one example, a video screen 762 is directly mounted to the handle 716. The video screen 762 may comprise an LCD screen. In other embodiments, the video screen 762 may comprise an OLED screen. It is further noted that the control pad 404 may be consolidated with the video screen 762, such that menu options are provided and selectable through touch-screen features.

In view of the arrangement of the endoscope 700, the shaft 704 with the coupling mechanism forms a modular element that they can be readily connected to one of multiple handles. In this respect, the shaft 704 is versatile.

In view of the above detachable shaft flexible endoscope 100, a method of using this medical instrument is disclosed. Starting with the flexible shaft 104 and the handle 102 in detached configuration, a user mates a first component 114*a* of the coupling mechanism 114 with a second component 114*b* of the coupling mechanism 114, and locks the two components securely together using a lock mechanism 118. During the engagement process, the flexible shaft 104 and the handle 102 align and couple with each other along the longitudinal axis 112 while the pins 302*b*, 304*b* connect with the contact regions 302*a*, 304*a*. Once the lock 118 is engaged, the flexible shaft 104 and handle 102 are securely fixed to each other. The user then checks to see if any fluid previously entered into the interior of the shaft 104, using the check valve 124. The user may then discharge any foreign fluid through the check valve. At this point, the user can begin using the endoscope 100 to examine a body cavity. Once the surgeon has finished using the endoscope 100, it can be reprocessed and made sanitary either in an attached or detached configuration.

While the invention has been specifically described in connection with certain specific embodiments thereof, it is to be understood that this is by way of illustration and not of limitation and that various changes and modifications in form and details may be made thereto, and the scope of the appended claims should be construed as broadly as the prior art will permit.

What is claimed is:

1. A flexible endoscope, comprising:
 a handle having a first sealed enclosure for internal components of said handle;
 a flexible shaft having a distal end and a proximal end, said flexible shaft having a second sealed enclosure for internal components of said flexible shaft;
 a coupling mechanism releasably attaching said handle to the proximal end of said flexible shaft;
 an illumination unit disposed in the second sealed enclosure of said flexible shaft, said illumination unit providing light to an area in front of the distal end of said flexible shaft;
 an imaging unit disposed in the second sealed enclosure of said flexible shaft, said imaging unit generating image data of the area in front of the distal end of said flexible shaft; and
 a check valve mounted directly on said a proximal end of said flexible shaft such that said check valve is part of said flexible shaft, said check valve being configured to communicatively connect an interior of said second sealed enclosure having said illumination unit and imaging unit to outside and indicate a presence of fluid in the interior and release said fluid;
 wherein said coupling mechanism includes an electrical channel for transmitting electrical power to said illumination unit and said imaging unit, and a data channel for transmitting the image data from said imaging unit;
 wherein said first and second sealed enclosures respectively seal off fluid-tight said internal components of said handle and said flexible shaft from outside in a coupled state and a decoupled state of the endoscope.

2. The flexible endoscope of claim 1, wherein said check valve is adapted to releasably connect to a pump for removing said fluid from the interior of said shaft.

3. The flexible endoscope of claim 1, wherein said shaft further comprises a vent valve, said vent valve being adapted to adjust the pressure of the interior of said shaft.

4. The flexible endoscope of claim 3, wherein said vent valve maintains said interior and outside equally in pressure.

5. The flexible endoscope of claim 1, wherein said coupling mechanism comprises a first component disposed on the proximal end of the flexible shaft and a second component disposed on the handle, said first component and second component having complimentary shapes, wherein said first component interlocks with said second component to create a secure attachment therebetween.

6. The flexible endoscope of claim 5, wherein the first component forms a first seal with said shaft and said second component forms a second seal with said handle, said first and second seals independently reduce the likelihood of fluid being communicated into an interior of said shaft and an interior of said handle, respectively.

7. The flexible endoscope of claim 5, wherein said first component bears on said second component to create an external seal, said external seal reducing the likelihood that fluid is communicated into a region between the shaft and the handle.

8. The flexible endoscope of claim 1, further comprising a controller disposed in the handle, said controller receiving the image data for processing into a data format for display and sending a control signal for adjusting an image quality of said imaging unit through said data channel.

9. The flexible endoscope of claim 1, wherein the illumination unit comprises:
 at least one light emitting diode (LED) disposed at the proximal end of said flexible shaft;
 a light-transmitting fiber bundle extending between the LED and the distal end of said flexible shaft, said light-transmitting fiber bundle transmitting light from said LED; and
 a power cable transmitting electrical power from the electrical channel of said coupling mechanism to the LED.

10. The flexible endoscope of claim 1, wherein said illumination unit comprises:

at least one light emitting diode (LED) disposed at the distal end of the shaft; and
a power cable transmitting electrical power from the electrical channel of said coupling mechanism to the LED.

11. The flexible endoscope of claim 1, wherein said imaging unit comprises:
an image sensor disposed at the distal end of said flexible shaft, said image sensor captures an image of the area in front of the distal end of said flexible shaft and generates said image data; and
an image-transmitting cable for transmitting said image data to the data channel of said coupling mechanism.

12. The flexible endoscope of claim 11, wherein the image sensor is a solid state image sensor.

13. The flexible endoscope of claim 1, further comprising:
an articulation unit disposed in said flexible shaft, said articulation unit being adapted to bend a distal portion of said flexible shaft in a plane; and
a steering control disposed on said flexible shaft proximate to said proximal end, said steering control controlling the bending of the distal portion of said flexible shaft.

14. The flexible endoscope of claim 13, wherein the articulation unit includes at least one tension wire coupled to the distal end of the flexible shaft and extending to the steering control; and
wherein the steering control is movable, said movement adjusts a tension in the tension wire, and said adjustment of tension controls the bending of the distal portion of said flexible shaft.

15. The flexible endoscope of claim 1, wherein said flexible shaft has an inlet port positioned at the proximal end, an outlet port formed in the distal end, and a working channel extending between said inlet port and said outlet port, said working channel providing passage for fluid or a medical instrument.

16. A flexible endoscope system comprising:
a flexible shaft having a distal end and a proximal end, said flexible shaft having a sealed enclosure for internal components of said flexible shaft;
a coupling mechanism releasably attaching the proximal end of said flexible shaft to one of a plurality of handles, wherein each handle has a sealed enclosure for internal components of said handle;
an illumination unit in the sealed enclosure of said flexible shaft providing light to an area in front of the distal end of said flexible shaft;
an imaging unit in the sealed enclosure of said flexible shaft generating image data of the area in front of the distal end of said flexible shaft; and
a check valve mounted directly on said proximal end of said flexible shaft such that said check valve is part of said flexible shaft, said check valve being configured to communicatively connect an interior of the sealed enclosure of said flexible shaft having said illumination unit and imaging unit to outside and indicate a presence of fluid in the interior and release said fluid;
wherein said coupling mechanism includes an electrical channel for transmitting electrical power to said illumination unit and said imaging unit, and a data channel for transmitting the image data from said imaging unit to said handle;
wherein each of said plurality of handles is adapted to communicate said image data to an auxiliary device; and
wherein said sealed enclosure of each of said plurality of handles and said sealed enclosure of said flexible shaft respectively seal off fluid-tight said internal components of said respective handle and said flexible shaft from outside, in a coupled state and a decoupled state of the endoscope system.

17. The flexible endoscope system of claim 16, wherein said coupling mechanism comprises a first component disposed on the proximal end of the flexible shaft and a second component disposed on each of said plurality of handles, said first component and second components having complimentary shapes, wherein said first component interlocks with the second component of said one of the plurality of handles to create a secure attachment therebetween.

18. The flexible endoscope system of claim 17, wherein said first component bears on said second component to create an external seal, said external seal reducing the likelihood that fluid is communicated into a region between the shaft and the handle.

19. The flexible endoscope system of claim 16, further comprising:
an articulation unit disposed in said flexible shaft, said articulation unit being adapted to bend a distal portion of said flexible shaft in a plane; an
a steering control disposed on said flexible shaft proximate to said proximal end, said steering control controlling the bending of the distal portion of said flexible shaft.

20. The flexible endoscope system of claim 16, further comprising a controller disposed in the handle, said controller receiving the image data for processing into a data format for display and sending a control signal for adjusting an image quality of said imaging unit through said data channel.

21. The flexible endoscope system of claim 20, wherein said auxiliary device is adapted to control said controller to adjust an image quality of said imaging unit.

22. The flexible endoscope system of claim 20, wherein the one of said plurality of handles comprises a cable adapted to plug into said auxiliary device, said cable providing communication between said auxiliary device and said controller and providing transmission of said electrical power from said auxiliary device to said handle and said coupling mechanism; and
wherein said auxiliary device processes said image data for display on a monitor.

23. The flexible endoscope system of claim 22, wherein said auxiliary device comprises a camera control unit.

24. The flexible endoscope system of claim 22, wherein said auxiliary device comprises a computer.

25. The flexible endoscope system of claim 20, wherein the one of said plurality of handles comprises:
an internal battery source for providing said electrical power to said illumination unit and said imaging unit; and
a transmitter-receiver for wirelessly communicating with said auxiliary device, wherein said auxiliary device processes said image data for display on a monitor.

26. The flexible endoscope system of claim 20, wherein the one of said plurality of handles comprises:
an internal battery source for providing said electrical power to said illumination unit and said imaging unit; and
an integrated video screen for displaying said image data, said video screen being said auxiliary device.

* * * * *